(12) United States Patent
Yadav et al.

(10) Patent No.: US 10,788,672 B2
(45) Date of Patent: Sep. 29, 2020

(54) AUGMENTED VISUALIZATION DURING SURGERY

(71) Applicant: MIRUS LLC, Atlanta, GA (US)

(72) Inventors: Jay Yadav, Sandy Springs, GA (US); Angad Singh, Atlanta, GA (US)

(73) Assignee: MiRus LLC, Marietta, GA (US)

( * ) Notice: Subject to any disclaimer, the term of this patent is extended or adjusted under 35 U.S.C. 154(b) by 0 days.

(21) Appl. No.: 16/081,590

(22) PCT Filed: Mar. 1, 2017

(86) PCT No.: PCT/US2017/020176
§ 371 (c)(1),
(2) Date: Aug. 31, 2018

(87) PCT Pub. No.: WO2017/151752
PCT Pub. Date: Sep. 8, 2017

(65) Prior Publication Data
US 2019/0011709 A1  Jan. 10, 2019

Related U.S. Application Data

(60) Provisional application No. 62/301,729, filed on Mar. 1, 2016.

(51) Int. Cl.
*G06T 5/00* (2006.01)
*G02B 27/01* (2006.01)
(Continued)

(52) U.S. Cl.
CPC .......... *G02B 27/0172* (2013.01); *A61B 34/10* (2016.02); *A61B 90/37* (2016.02);
(Continued)

(58) Field of Classification Search
CPC ...... A61B 5/0496; G06F 3/012; G06T 19/006
(Continued)

(56) References Cited

U.S. PATENT DOCUMENTS

| 8,504,136 B1 | 8/2013 | Sun et al. |
| 8,657,809 B2 | 2/2014 | Schoepp |

(Continued)

FOREIGN PATENT DOCUMENTS

| DE | 102012025374 A1 | 7/2014 |
| WO | 2005088539 A2 | 9/2005 |

(Continued)

OTHER PUBLICATIONS

Suenaga et al. "Vision-based markerless registration using stereo vision and an augmented reality surgical navigation system: a pilot study," 2015, BMC Medical Imaging.

(Continued)

*Primary Examiner* — Thomas J Lett
(74) *Attorney, Agent, or Firm* — Meunier Carlin & Curfman LLC

(57) ABSTRACT

An example augmented reality (AR) system can include a frame, a lens attached to the frame, and a plurality of cameras attached to the frame. The cameras can be configured to record a real-time image. Optionally, the real-time image can include a portion of a subject's body and/or one or more surgical instruments. Additionally, the AR system can include a plurality of inertial measurement units, where a respective inertial measurement unit is attached to each respective camera. Optionally, the AR system can be configured to display image data (e.g., medical image data) registered and superimposed on the real-time image as seen by the user of the AR system.

42 Claims, 4 Drawing Sheets

(51) Int. Cl.
| | |
|---|---|
| *G06F 3/01* | (2006.01) |
| *A61B 34/10* | (2016.01) |
| *A61B 90/00* | (2016.01) |
| *G06T 11/60* | (2006.01) |
| *G06T 19/00* | (2011.01) |
| *G06F 3/14* | (2006.01) |

(52) U.S. Cl.
CPC ........... G02B 27/017 (2013.01); G06F 3/012 (2013.01); G06T 11/60 (2013.01); G06T 19/006 (2013.01); *A61B 2034/107* (2016.02); *A61B 2090/363* (2016.02); *A61B 2090/365* (2016.02); *A61B 2090/371* (2016.02); *A61B 2090/374* (2016.02); *A61B 2090/376* (2016.02); *A61B 2090/378* (2016.02); *A61B 2090/3762* (2016.02); *G02B 2027/014* (2013.01); *G02B 2027/0138* (2013.01); *G02B 2027/0141* (2013.01); *G02B 2027/0178* (2013.01); *G06F 3/14* (2013.01); *G06T 2210/41* (2013.01); *G09G 2380/08* (2013.01)

(58) Field of Classification Search
USPC .......................................................... 345/419
See application file for complete search history.

(56) References Cited

U.S. PATENT DOCUMENTS

| | | | |
|---|---|---|---|
| 9,123,155 | B2 | 9/2015 | Cunningham et al. |
| 2011/0282140 | A1* | 11/2011 | Itkowitz ................ G06T 19/006 600/109 |
| 2012/0209123 | A1 | 8/2012 | King |
| 2014/0111623 | A1 | 4/2014 | Zhao et al. |
| 2014/0275760 | A1 | 9/2014 | Lee et al. |
| 2015/0235435 | A1* | 8/2015 | Miller ................... G06T 19/006 345/633 |
| 2016/0225192 | A1* | 8/2016 | Jones ...................... G06F 3/012 |
| 2016/0270656 | A1* | 9/2016 | Samec .................. A61B 5/0496 |

FOREIGN PATENT DOCUMENTS

| | | |
|---|---|---|
| WO | 2012158801 A2 | 11/2012 |
| WO | 2013176525 A1 | 11/2013 |
| WO | 2015145395 A1 | 10/2015 |

OTHER PUBLICATIONS

Gilson et al., "Spatial calibration of an optical see-through head mounted display," 2008, J Neurosci Methods, vol. 173(1), pp. 140-146.

Jung, S., "Augmented Reality Surgery: How a Mobile Device Can You're Life" 2014, available at https://iq.intel.com/how-a-mobile-device-can-save-your-life-augmented-reality-surgery/ (accessed Aug. 2018).

Chen et al., "Development of a surgical navigation system based on augmented reality using an optical see-through head-mounted display," 2015, J. Biomedical Informatics, vol. 55, pp. 124-131.

Spinal News International, "Precision insertion of sacroiliac screws using an augmented reality-based navigation system is feasible and accurate," Jan. 2016.

Shenzhen Yamay Digital Electronics Co. Ltd, wearable digital bluetooth smart glasses, available at http://yamaytech.en.alibaba.com (accessed Jan. 2016).

Vuzix AR glasses with stereo cameras, available at http://www.gizmag.com/vuzix1200araugmentedrealityglasses/26264/ (accessed Jan. 2016).

Tao Zu, "AR Optics—Is Waveguide Lighting the Way?", Jan. 2017, available at https://www.linkedin.com/pulse/ar-optics-waveguide-lighting-way-tao-xu-%E5%BE%90%E6%B6%9B-3/1/2017/ (accessed Jan. 2017).

International Search Report and Written Opinion issued in related International Application No. PCT/US2017/020176 dated May 19, 2017.

* cited by examiner

AUGMENTED VISUALIZATION DURING SURGERY

CROSS-REFERENCE TO RELATED APPLICATIONS

This application is a national stage application filed under 35 U.S.C. § 371 of PCT/US2017/020176 filed Mar. 1, 2017, which claims the benefit of U.S. Provisional Patent Application No. 62/301,729, filed on Mar. 1, 2016, entitled "AUGMENTED VISUALIZATION DURING SURGERY," the disclosures of which are expressly incorporated herein by reference in their entireties.

BACKGROUND

Augmented reality systems provide users with a view of the real world supplemented (i.e., augmented) by computer-generated content.

Many orthopedic surgeries, such as those involving the spine, are complex procedures that require a high degree of precision. For example, the spine is in close proximity to delicate anatomical structures such as the spinal cord and nerve roots. Compounding the problem is limited surgical exposure and visibility, particularly in the case of minimally invasive procedures. Consequently, the risk of misplaced implants or other complications is high.

Similarly, in orthopedic procedures involving resurfacing, replacement, or reconstruction of joints using multi component prosthesis with articulating surfaces, proper placement of the prosthetic component is critical for longevity of the implant, positive clinical outcomes, and patient satisfaction.

Currently, many orthopedic surgeons intra-operatively evaluate prosthetic component placement using an imprecise combination of subjective experience of the surgeon and rudimentary mechanical instrumentation. In certain surgeries involving complex anatomies, such as spine surgery, the surgeon may rely on intraoperative imaging to guide and assess the placement of prosthesis. However imaging is typically not real-time and has to be repeated whenever there is movement of the anatomy and/or surgical instrument thereby exposing the patient and surgical team to harmful radiation over the duration of the procedure.

Some computer/robotically-assisted surgical systems provide a platform for more reliably estimating prosthetic placement parameters. These systems typically require complex and sophisticated tracking equipment, bulky markers/sensors, time-consuming instrument calibration/registration procedures, and highly-specialized software packages that often require technical support personnel to work with doctor in the operating room. Not only do such systems tend to be costly, they also tend to be far too complex to warrant broad adoption among orthopedic surgeons.

To provide a cost-effective and relatively user-friendly approach that is unavailable in typical computer/robotically-assisted systems, a cost-effective, and user-friendly tool for visualizing and guiding prosthetic component positioning would be advantageous, particularly if it minimizes the amount of capital equipment, procedural steps, and radiation exposure for the patient and surgical team. The presently disclosed augmented reality system for visualizing the anatomy and surgical instruments in real-time are directed to overcoming one or more of the problems set forth above and/or other problems in the art.

SUMMARY

An example augmented reality (AR) system can include a frame, a lens attached to the frame, and a plurality of cameras attached to the frame. The frame can be worn by a user, e.g., the frame can be a wearable frame. Optionally, the frame can be made of a flexible material, and/or the lens can be at least partially transparent. The cameras can be configured to record a real-time image. For example, the real-time image can be of the scene in the field of view of the cameras, e.g., a scene in proximity to the wearer (or user) of the AR system. In some implementations, the real-time image can be a three-dimensional (3D) image generated in visible light. In other implementations, the real-time image can be a 3D image generated in light at other wavelengths such as IR. In yet other implementations, the real-time image can be a 3D image generated in visible light and light at other wavelengths. Optionally, the real-time image can include a portion of a subject's body. Additionally, the AR system can include a plurality of inertial measurement units, where a respective inertial measurement unit can be attached to each respective camera. Each inertial measurement unit can include at least one of a gyroscope, an accelerometer, or a magnetometer.

Additionally, in some implementations, the AR system can include a plurality of photosensors (e.g., light-detecting devices) such as photodiodes, for example, attached to the frame and/or the each respective camera. Alternatively or additionally, the AR system can include a plurality of light-emitting and/or light-reflecting elements, for example, attached to the frame and/or the each respective camera. Optionally, the light-emitting elements can be light-emitting diodes.

In some implementations, the cameras can be arranged in a spaced apart relationship on the frame. Additionally, a respective field of view of each of the cameras can intersect with one another.

Alternatively or additionally, in some implementations, the AR system can include a computing device. The computing device can optionally be attached to the frame. Alternatively, the computing device can optionally be separate from or external to the frame. The computing device can include a processor and a memory operably coupled to the processor.

Alternatively or additionally, in some implementations, the AR system can further include an optical projector attached to the frame or the lens. Optionally, the lens can include a waveguide such that the lens and optical projector form a projection microdisplay.

Alternatively or additionally, the AR system can further include a display device (e.g., LCD or LED display) attached to the frame or the lens.

Alternatively or additionally, in some implementations, the AR system can further include a speaker and/or microphone to receive and/or provide audio information.

In some implementations, the computing device can be configured to receive a respective signal from each of the inertial measurement units, calculate a respective pose (i.e., position and orientation) of each of the cameras relative to a reference coordinate system, and apply a correction to the real-time image based on the respective pose of each of the cameras.

Alternatively or additionally, in some implementations, the computing device can be configured to receive image data related to a portion of a subject's body, and to register the image data with the real-time image. The registered image data can then be superimposed with the real-time image and displayed to the user, for example, using the lens, display, and/or optical projector. This disclosure contemplates that the image data can be registered with the real-time image based on a fiducial marker that appears in the image data and the real-time image. Additionally, the image data can be registered with the real-time image using a registration algorithm. Alternatively or additionally, the computing device can be configured to track pose changes of an object of interest (e.g., an anatomic structure, surgical instrument, etc.) in the real-time image. It should be understood that such tracking can be accomplished in real time. The computing device can be configured to update the image data based on the tracked pose changes. The computing device can also be configured to merge or superimpose the updated image data with the real-time image.

In some implementations, the image data can include virtual anatomic models, virtual surgical instruments, trajectories and angles obtained via virtual surgical planning, and/or an anatomic structure such as a blood vessel, a nerve, or a bone. Alternatively or additionally, the image data can include a template obtained from one or more images of a portion of the subject or obtained from literature. Image data can also include display of information such as measurements and angles related to the real-time image. As described above, the image data can be superimposed with the real-time image. Optionally, the image data can be two-dimensional or three-dimensional image data. In some implementations, the three-dimensional image data can be of an anatomic structure (e.g., bones, soft tissue, etc.) that is not visible in the surgical field. For example, the image data can be magnetic resonance image (MRI), computed tomography (CT), ultrasound, or fluoroscopic image data.

Alternatively or additionally, in some implementations, the computing device can be configured to receive pose data (i.e., position and orientation data) related to a surgical instrument and/or an anatomic feature relative to the portion of the subject's body. The computing device can also be configured to update the image data with the pose data. The updated image data can be registered with the real-time image. The updated image data can then be displayed via the lens or display. The pose data can be obtained by one or more cameras in the AR system that localizes and tracks natural or artificial features (e.g. fiducial markers) present in the real-time image such as fiducial markers fixed to/on a portion of the subject's body and/or a surgical instrument. Alternatively, the pose data can be obtained from a separate tracking system such as an optical or electromagnetic (EM) tracking system. The tracking system can also optionally track the pose of the AR device.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for an example AR system for visualization during surgery, it will become evident to those skilled in the art that the implementations are not limited thereto, but are applicable for AR visualization in other environments.

Example AR System

Figure 1A:
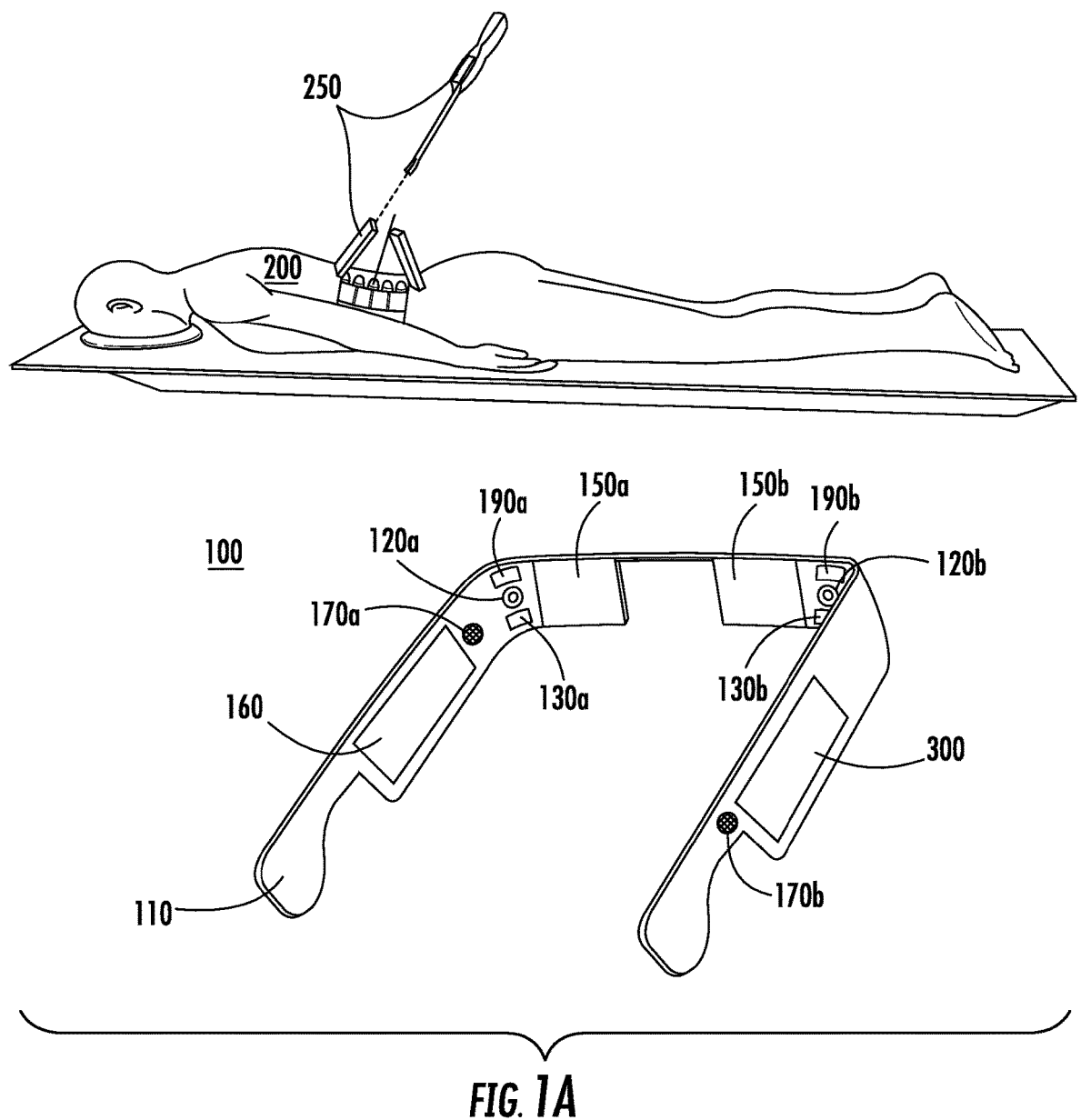
FIG. 1A is a view of another example AR system as described herein.

Referring now to FIG. 1A, an example AR system 100 is shown. The AR system 100 can include a frame 110, a lens 150a, 150b attached to the frame 110 (collectively referred to herein as lens 150), and a plurality of cameras 120a, 120b (collectively referred to herein as cameras 120) attached to the frame 110. The cameras 120 can be arranged in a spaced apart relationship on the frame 110. Optionally, the cameras 120 can be a lightweight, compact device configured to capture digital images, e.g., a digital video camera. For example, this disclosure contemplates that any commercially available high definition (HD) digital video cameras such as the PANASONIC HX-A1 of PANASONIC CORP. of Kadoma, Japan can be used. In addition, cameras 120 can be one or more depth cameras such as a Time of flight (ToF) camera or a RGB-D camera. An RGB-D camera is an RGB camera that augments its image with depth information. Examples of such cameras such as the SWISS RANGER 5R4000/4500 from MESA IMAGING of Zurich, Switzerland and CARMIN AND CAPRI series cameras from PRIMESENSE of Tel Aviv, Israel. The cameras 120 can be configured to record a real-time image (also sometimes referred to as the real-time 3D image).

Figure 1B:
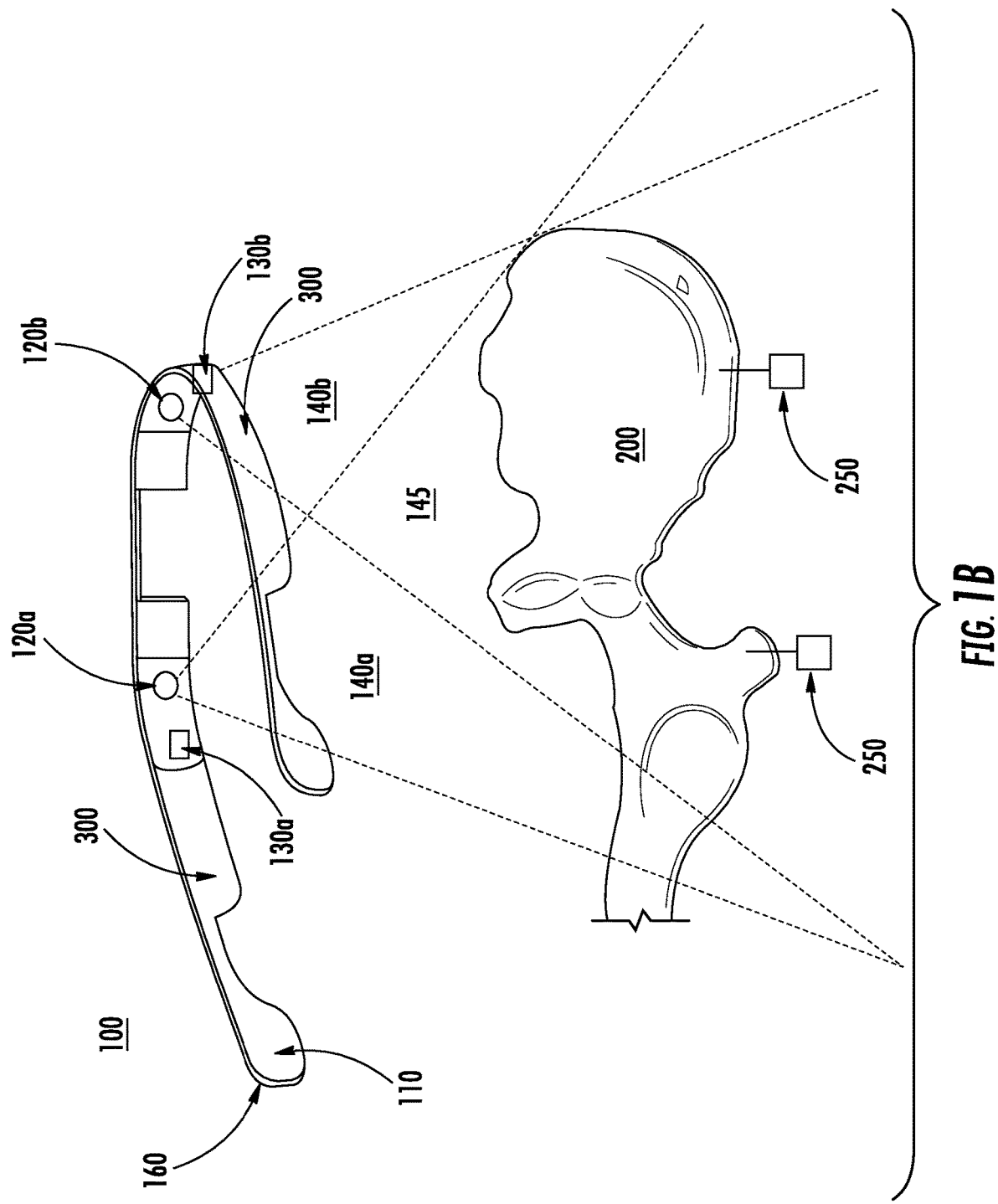
FIG. 1B is a view of an example AR system as described herein.

Referring now to FIG. 1B, another example AR system 100 is shown. Similar to the AR system of FIG. 1A, the AR system 100 can include a frame 110, and a plurality of cameras 120a, 120b (collectively referred to herein as cameras 120) attached to the frame 110. The cameras 120 can be arranged in a spaced apart relationship on the frame 110. As shown in FIG. 1B, a respective field of view 140a, 140b of each of the cameras 120 intersect with one another (e.g., as shown by the intersecting field of view 145 of FIG. 1B).

Referring now to FIGS. 1A and 1B, the real-time image can include a portion of a subject's body 200 (e.g., the subject's spine as shown in FIG. 1A or the subject's pelvis as shown in FIG. 1B). Additionally, the AR system 100 can include a plurality of inertial measurement units 130a, 130b (referred to herein as inertial measurement units or module 130), where a respective inertial measurement unit 130 may be attached to each respective camera 120a, 120b. Each inertial measurement unit 130 can include at least one of a gyroscope, an accelerometer, or a magnetometer. The inertial measurement unit 130 is described below with regard to FIG. 2.

Optionally, the frame 110 can be made of a flexible material. In other words, the frame 110 is capable of being deformed. It should be understood that when the frame 110 deforms, the relative orientation of each of the cameras 120 changes. Accordingly, as described below, it is possible to correct the real-time image using measurements obtained by the inertial measurement units 130. Alternatively or additionally, by analyzing images of fixed reference fiducial markers 250 in the field of view, it is possible to determine relative pose (i.e., position and orientation) between the cameras to further assist with the correction. Alternatively or additionally, using pairs of light-emitting, light-reflecting, and/or light-detecting devices attached to each respective camera, it is possible to determine relative pose (i.e., position and orientation) between the cameras to further assist with the correction. Alternatively or additionally, magnetometers attached to each respective camera can provide similar information. The above independent pieces of information can be "fused" to arrive at a more accurate estimate of the relative pose between the respective cameras than would be possible with each individual measurements. Lens 150 in AR system 100 of FIG. 1A is at least partially transparent. In some implementations, the lens can be completely transparent. In some implementations, the lens can be partially transparent, e.g., colored, polarized, etc. The lens can be configured for see-through AR viewing such that the user (e.g., the person wearing the AR system 100) can see the real world while simultaneously viewing computer-generated content (described below).

Alternatively or additionally, the AR system 100 can include a computing device 300. In some implementations, the computing device 300 can be attached to the frame 110 (e.g., as shown in FIGS. 1A and 1B). In some implementations, the computing device 300 can be external to or separate from the frame 110. In this implementation, the computing device 300 can be communicatively coupled with the components attached to the frame by a communication link (e.g., any wired or wireless communication link). Optionally, as shown in FIG. 1B, the AR system 100 can include a plurality of computing devices, e.g., a computing device corresponding to each of the cameras 120. This disclosure contemplates that the AR system 100 can include more or less than two computing devices (e.g., a single computing device as shown in FIG. 1A). The computing device 300 can include one or more processors (e.g. CPU, GPU) and a memory operably coupled to the processor and is described below with regard to FIG. 3. The computing device 300 can be configured to receive a respective signal from each of the inertial measurement units 130 and/or cameras 120, calculate a respective orientation of each of the cameras 120 relative to a reference coordinate system, and apply a correction to the real-time image based on the respective orientation of each of the cameras 120. Algorithms for calculating orientation of an object (e.g., a camera) using inertial sensor measurements are known in the art. This disclosure contemplates using any known process to calculate orientation of the cameras 120. Additionally, algorithms for correcting a real-time image based on orientation of a camera are known in the art. This disclosure contemplates using any known process to correct a real-time image based on orientation of the cameras.

In some implementations, the AR system 100 can include a power source 160 such as a battery, fuel cell, MEMs micro-generator, or any other suitable compact power supply. As shown in FIGS. 1A and 1B, the power source 160 can be attached to the frame 110. Alternatively or additionally, the AR system 100 can optionally include a microphone 170a and/or a speaker 170b as shown in FIG. 1A. In some implementations, the AR system 100 can further include a near eye display 190a, 190b (collectively referred to herein as "near eye display") as shown in FIG. 1A. In FIG. 1A, a near eye display 190 is provided for each lens 150. The near eye display 190 can be attached to the frame 110 and/or the lens 150. It should be understood that the configuration for the near eye display 190 shown in FIG. 1A is provided only as an example. This disclosure contemplates that the near eye display 190 can be a display device or a projector microdisplay. Projector microdisplays are known in the art and can include, but are not limited to, half-mirror, prism-based, waveguide-based, and retinal scanning projector microdisplays. The lens 150 can include a waveguide when using a waveguide-based projector microdisplay. Waveguide-based microdisplays are known in the art. For example, light from an optical projector can be reflected (e.g., by a hologram) such that the light passes into the waveguide, which can be incorporated in the lens 150. After travelling through the waveguide, the light can be reflected (e.g., by another hologram) into the user's (e.g., person wearing AR system 100) eye. In some implementations, the near eye display 190 can optionally be an optical projector attached to the frame 110 or the lens 150. The optical projector can be configured to project image data (e.g., X-ray data, virtual data, etc. as described herein) into a user's field of view (e.g., the field of view of the person wearing the AR system 100). In some implementations, the optical projector can be configured to project images onto the lens 150 of the AR system 100. An example of such an optical projector is the Waveguide Optics Engine of NOKIA of Espoo, Finland. In some implementations, the optical projector can be configured to project images onto a surface other than the lens. For example, the images can optionally be projected onto a half-silvered mirror arranged between the user (e.g., a surgeon or other medical professional wearing the AR system 100) and a subject undergoing a medical procedure. Alternatively, the images can optionally be projected directly onto the subject undergoing a medical procedure. An example of such an optical projector is the PICOP DISPLAY TECHNOLOGY of MICROVISION, INC. of Redmond, Wash. Alternatively or additionally, in some implementations, the near eye display 190 can optionally be a display device (e.g., LCD or LED display) attached to the frame 110 or the lens 150. In this implementation, the image data can be displayed on the display device (i.e., as opposed to projected onto the lens). It should be understood that the above examples allow a user to see the real world while simultaneously viewing the projected content.

The computing device 300 can be configured to receive image data related to a portion of a subject's body. The image data can optionally include an anatomic structure such as a blood vessel, a nerve, or a bone, for example. Optionally, the image data can be two-dimensional or three-dimensional image data. For example, the image data can be magnetic resonance image (MRI), computed tomography (CT), ultrasound, or fluoroscopic image data. Alternatively or additionally, the image data can optionally include a virtual anatomic model, a virtual anatomic template (e.g., obtained from image data of the subject or literature), a virtual surgical instrument, a virtual surgical planning trajectory or angle, and/or a surgical target (also referred to herein as "virtual data"). The computing device 300 can receive the image data from a remote computing device over a communication link. This disclosure contemplates the communication link is any suitable communication link. For example, a communication link can be implemented by any medium that facilitates data exchange between the network elements including, but not limited to, wired, wireless and optical links. Example communication links include, but are not limited to, a LAN, a WAN, a MAN, Ethernet, the Internet, or any other wired or wireless link such as Bluetooth, Wi-Fi, ZigBee, Wi-Max, 3G or 4G. The computing device 300 can be configured to register the image data with the real-time image. The computing device 300 can superimpose the registered image data with the real-time image. Additionally, the computing device 300 can track pose changes of an object of interest (e.g., an anatomic feature or other object) in real-time using the real-time image. The computing device 300 can optionally update the image data based on the tracked pose changes of the object of interest and then merge or superimpose the updated image data with the real-time image. The image data can be registered with the real-time image based on a fiducial marker 250 that appears in the image data and the real-time image. The fiducial marker can be an anatomic feature and/or an object (fiducial) placed into the imaging system's field of view. Additionally, the image data can be registered with the real-time image using a registration algorithm. Registration is a process known in the art and involves transforming data sets into a single coordinate system (e.g., a reference coordinate system) such as point matching, surface/object matching, palpation of anatomic landmarks, and processing of single plane or multi-plane intra-operative imaging. This disclosure contemplates using any known registration algorithms in the techniques described herein. The registered image data can then be projected for viewing by the user of the AR system 100, for example, using the lens 150 described above.

Alternatively or additionally, the computing device 300 can be configured to receive pose data related to a surgical instrument relative to the portion of the subject's body or relative pose data of different objects/anatomic features in the user's field of view. The pose data can be based at least in part on the analysis of the real-time image captured by cameras 120 of the object(s) of interest and/or fiducial markers 250 attached to the object(s) of interest (e.g., the subject's spine and surgical instrument in FIG. 1A or the subject's pelvis in FIG. 1B). For example, each image frame can be analyzed and processed using algorithms that detect and localize specific visual patterns of an object of interest and/or fiducial marker 250. The algorithms further analyze the projection of the pattern on the image plane and calculate the pose of object of interest and/or fiducial marker 250 in the real-world coordinates (e.g., a reference coordinate system). This final calculation relies in part on the calibration of the camera 120 which is performed prior to use. An example algorithm that performs the above sequence of operations in real-time is the open source AprilTag library (https://april-1.eecs.umich.edu/software/apriltag.html). It should be understood that AprilTag is only one example algorithm for processing images to detect and localize visual patterns of fiducial markers in order to calculate pose and that other processes may be used with the AR system described herein. Optionally, the pose data related to the surgical instruments, objects, anatomic features, etc. are obtained by an optical or electromagnetic (EM) tracking system. The tracking system can be separate from the AR system 100. The computing device 300 can be configured to update the image data based on the pose data and merge the image data with the real-time image.

It should be understood that image data (e.g., MRI, CT, etc.) and surgical instrument position data are only provided as examples of computer-generated content that can be projected for viewing by the user of the AR system 100. This disclosure contemplates that other content can be projected for viewing by the user of the AR system 100. The other content can include, but is not limited to, any information that may be relevant to the user of the AR system 100.

This disclosure contemplate that the superimposition of image data and/or pose data as described herein with the real-time image can be used in a number of applications. It should be understood that the applications described below are examples only and are not intended to be limiting. For example, a template (e.g., a template of an anatomic feature) can optionally be extracted from the image data (e.g., MRI, CT, etc. images) of the subject or a template can be obtained from literature. The computing device 300 can be configured to superimpose such a template on the real-time image, and the template and real-time image can be displayed to a user of the AR system 100.

Optionally, in some implementations, various anatomic structures such as nerves, arteries, veins, etc. can be identified. For example, it is possible to extract anatomic structures contained in the image data (e.g., MRI, CT, etc. images) of the subject or to identify anatomic structures using an imaging modality such as infrared (IR) imaging. Algorithms for extracting anatomic structures contained in image data are known in the art. This disclosure contemplates using any known process to extract anatomic structures contained in image data. This disclosure contemplates that the AR system 100 can include an IR camera or other device for capturing images, for example, attached to the frame 110 of the AR system 100. The computing device 300 can be configured to superimpose such anatomic structures on the real-time image, and the anatomic structures and real-time image can be displayed to a user of the AR system 100. Optionally, the computing device 300 can be configured to enhance the anatomic structure, for example, to facilitate differentiation between anatomic structures such as nerves, arteries, veins, etc. Algorithms for enhancing anatomic structures are known in the art. This disclosure contemplates using any known process to enhance anatomic structures.

Optionally, in some implementations, the image data can be a 3D image (e.g., ultrasound) of an anatomic structure (e.g., a soft tissue or organ) that is not visible to a surgeon or other medical professional in the surgical field. The computing device 300 can be configured to superimpose the 3D image with the real-time image, and the 3D image and real-time image can be displayed to a user of the AR system 100.

Optionally, in some implementations, the AR system 100 can be used for obtaining measurement, angulations, relationships, etc. between or among objects of interest within the surgical field. As described herein, the AR system 100 can configured to capture a real-time image of a portion of the subject, and image data can be superimposed on the real-time image. This disclosure contemplates that the computing device 300 can be configured to obtain measurements, angulations, relationships, etc. based on the real-time image and/or the superimposed data.

This disclosure contemplates that the applications described above can assist a surgeon or other medical professional during a medical procedure. For example, the AR system 100 can be used to provide guidance during such medical procedure. The AR system 100 can also provide qualitative information during the medical procedure. As discussed herein, it is possible to superimpose (and optionally enhance) different anatomic structures. In some implementations, these anatomic structures might not be visible to the surgeon in the surgical field. This can provide the surgeon with visual information about the location of and/or relationship between different anatomic structures such as soft tissues. The AR system 100 can also provide a way to simulate "what if" scenarios if various implants, surgical instruments, surgical technique, etc. are used. As described herein, the image data can include various virtual models, including virtual anatomic models/templates and/or virtual surgical planning trajectories or angles. By superimposing such data with the real-time image, the surgeon or other medical professional can virtually view or simulate various surgical options.

Example Inertial Measurement Unit

Figure 2:
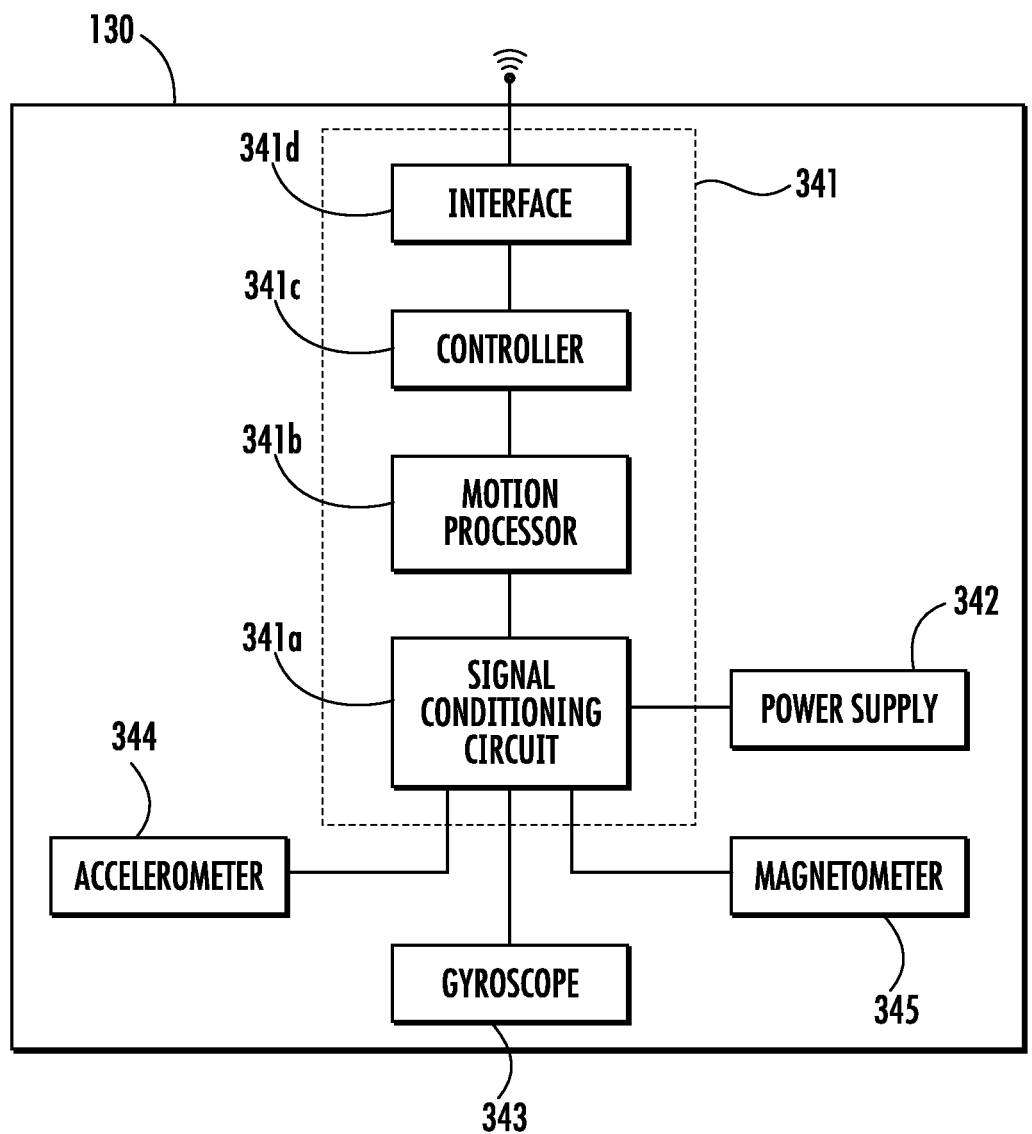
FIG. 2 is an example inertial measurement unit.

Referring now to FIG. 2, an example inertial measurement unit (IMU) 130 is shown. According to one implementation, IMUs can include or embody one or more of 3-axis gyroscopes and 3-axis accelerometers. The IMU's can also include 3-axis magnetometers or magnetic sensors. The IMU can measure linear and rotational motion in a reference coordinate frame or relative to a starting position or another IMU. They can also measure the strength and/or direction of a magnetic field, for example the strength and direction of the magnetic field emanating from a magnetic field generator. Inertial measurement units consistent with the disclosed implementations are described in greater detail below with respect to the schematic diagram of FIG. 2.

The inertial measurement unit 130 can be configured to communicate with each other and/or to a computing device (e.g., a computing device 300 of FIG. 3) using a wired or wireless connection. The wireless communication can be achieved via any medium that facilitates data exchange including any standard radio frequency communication protocol such Bluetooth, Wi-Fi, ZigBee, etc., or a custom protocol. In some implementations, wireless communication is achieved a wireless communication transceiver.

In some implementations, the accelerometers, gyroscopes, and magnetometer in the inertial measurement unit 130 work collectively to provide an accurate estimate of angular motion that can be processed to calculate orientation relative in a reference coordinate frame. The magnetometer can also measure the direction and intensity of a magnetic field. For example, 3-axis magnetometers can be used to measure the direction and intensity of the magnetic field emanating from a magnetic field generator. For example the magnetic field generator can be a permanent magnet or electromagnet (i.e. a wound coil through which current is passed). In the case of an electromagnet, one or more coils can be utilized to create multiple magnetic fields that are at known orientations to each other.

Inertial measurement unit 130 can also include one or more subcomponents configured to detect and transmit information that either represents the 3-dimensional pose or can be used to derive the pose of the inertial measurement unit 130 (and, by extension, any object that is affixed relative to inertial measurement unit 130, such as the cameras 120 and/or frame 110). Inertial measurement unit 130 can embody a device capable of determining a 3-dimensional pose associated with any body to which inertial measurement unit 130 is attached. According to one implementation, orientation sensor(s) in inertial measurement unit 130 can be an inertial measurement unit including a microprocessor 341, a power supply 342, and one or more of a gyroscope 343, an accelerometer 344, or a magnetometer 345.

According to one implementation, the inertial measurement unit 130 can contain a 3-axis gyroscope 343, a 3-axis accelerometer 344, and a 3-axes magnetometer 345. It is contemplated, however, that fewer of these devices with fewer axes can be used without departing from the scope of the present disclosure. For example, according to one implementation, inertial measurement unit 130 can include only a gyroscope and an accelerometer, the gyroscope for calculating the orientation based on the rate of rotation of the device, and the accelerometer for measuring earth's gravity and linear motion, the accelerometer providing corrections to the rate of rotation information (based on errors introduced into the gyroscope because of device movements that are not rotational or errors due to biases and drifts). In other words, the accelerometer can be used to correct the orientation information collected by the gyroscope. Similarly the magnetometer 345 can be utilized to measure a magnetic field and can be utilized to further correct gyroscope errors. Thus, while all three of gyroscope 343, accelerometer 344, and magnetometer 345 can be used, orientation measurements can be obtained using as few as one of these devices. The use of additional devices increases the resolution and accuracy of the orientation information and, therefore, can be advantageous when orientation accuracy is important.

As illustrated in FIG. 2, microprocessor 341 of inertial measurement unit 130 can include different processing modules or cores, which can cooperate to perform various processing functions. For example, microprocessor 341 can include, among other things, an interface 341d, a controller 341c, a motion processor 341b, and signal conditioning circuitry 341a. Controller 341c can be configured to control the magnetic field generator which could be based on instructions received from the computing device 300 via interface 341d. Controller 341c can also be configured to control and receive conditioned and processed data from one or more of gyroscope 343, accelerometer 344, and magnetometer 345 and transmit the received data to one or more remote receivers. The data can be pre-conditioned via signal conditioning circuitry 341a, which includes amplifiers and analog-to-digital converters or any such circuits. The signals can be further processed by a motion processor 341b. Motion processor 341b can be programmed with so-called "motion fusion" algorithms to collect and process data from different sensors to generate error corrected orientation information. The orientation information can be a mathematically represented as an orientation or rotation quaternion, Euler angles, direction cosine matrix, rotation matrix of any such mathematical construct for representing orientation known in the art. Accordingly, controller 341c can be communicatively coupled (e.g., wirelessly via interface 341d as shown in FIG. 2, or using a wireline protocol) to, for example, computing device 300 and can be configured to transmit the orientation data received from one or more of gyroscope 343, accelerometer 344, and magnetometer 345 to computing device 300, for further analysis.

Interface 341d can include one or more components configured to transmit and receive data via a communication network, such as a wide area network, the Internet, a local area network, a workstation peer-to-peer network, a direct link network, a wireless network, or any other suitable communication platform. For example, interface 341d can include one or more modulators, demodulators, multiplexers, demultiplexers, network communication devices, wireless devices, antennas, modems, and any other type of device configured to enable data communication via a communication network. According to one implementation, interface 341d can be coupled to or include wireless communication devices, such as a module or modules configured to transmit information wirelessly using Wi-Fi or Bluetooth wireless protocols. As illustrated in FIG. 2, inertial measurement unit 130 can be powered by power supply 342, such as a battery, fuel cell, MEMs micro-generator, or any other suitable compact power supply.

Importantly, although microprocessor 341 of inertial measurement unit 130 is illustrated as containing a number of discrete modules, it is contemplated that such a configuration should not be construed as limiting. Indeed, microprocessor 341 can include additional, fewer, and/or different modules than those described above with respect to FIG. 2, without departing from the scope of the present disclosure. Furthermore, in other instances of the present disclosure that describe a microprocessor are contemplated as being capable of performing many of the same functions as microprocessor 341 of inertial measurement unit 130 (e.g., signal conditioning, wireless communications, etc.) even though such processes are not explicitly described with respect to microprocessor 341. Those skilled in the art will recognize that many microprocessors include additional functionality (e.g., digital signal processing functions, data encryption functions, etc.) that are not explicitly described here. Such lack of explicit disclosure should not be construed as limiting. To the contrary, it will be readily apparent to those skilled in the art that such functionality is inherent to processing functions of many modern microprocessors, including the ones described herein.

Microprocessor 341 can be configured to receive data from one or more of gyroscope 343, accelerometer 344, and magnetometer 345, and transmit the received data to one or more remote receivers. Accordingly, microprocessor 341 can be communicatively coupled (e.g., wirelessly (as shown in FIG. 2, or using a wireline protocol) to, for example, computing device 300 and configured to transmit the orientation and position data received from one or more of gyroscope 343, accelerometer 344, and magnetometer 345 to computing device 300, for further analysis. As illustrated in FIG. 2, microprocessor 341 can be powered by power supply 342, such as a battery, fuel cell, MEMs microgenerator, or any other suitable compact power supply.

Example Computing Device

It should be appreciated that the logical operations described herein with respect to the various figures may be implemented (1) as a sequence of computer implemented acts or program modules (i.e., software) running on a computing device (e.g., the computing device described in FIG. 3), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 3:
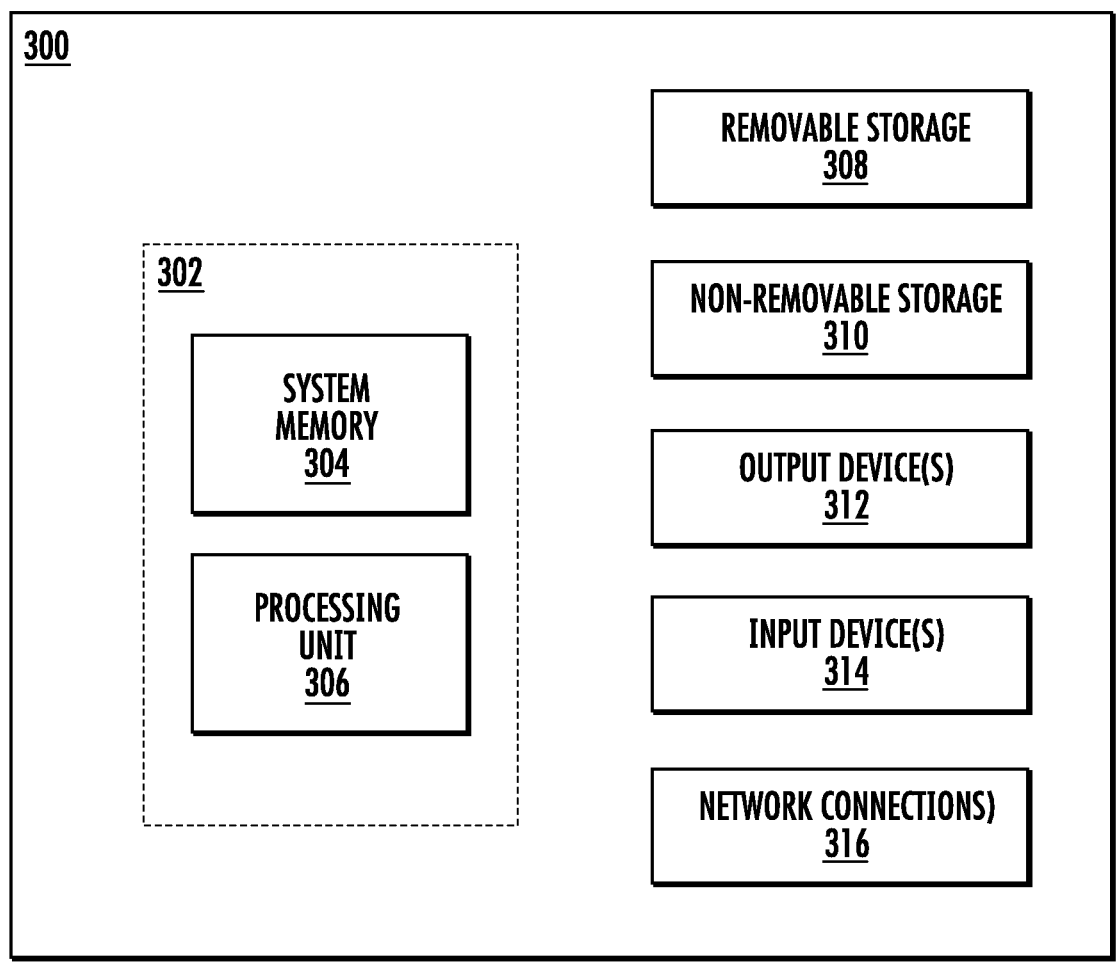
FIG. 3 is an example computing device.

Referring to FIG. 3, an example computing device 300 upon which embodiments of the invention may be implemented is illustrated. It should be understood that the example computing device 300 is only one example of a suitable computing environment upon which embodiments of the invention may be implemented. Optionally, the computing device 300 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

Computing device 300 can include or embody any suitable microprocessor-based device configured to process, analyze, and/or display image and pose information. According to one implementation, computing device 300 can be a general purpose computer programmed with software for receiving, processing, and displaying image and pose information. According to other implementations, computing device 300 can be a special-purpose computer, specifically designed to communicate with, and process information for, other components.

In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor such as a Central Processing Unit (CPU) and/or Graphics Processing Unit (GPU) that performs arithmetic and logic operations necessary for operation of the computing device 300. The computing device 300 may also include a bus or other communication mechanism for communicating information among various components of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, microphone etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Tangible, computer-readable media refers to any media that is capable of providing data that causes the computing device 300 (i.e., a machine) to operate in a particular fashion. Various computer-readable media may be utilized to provide instructions to the processing unit 306 for execution. Example tangible, computer-readable media may include, but is not limited to, volatile media, non-volatile media, removable media and non-removable media implemented in any method or technology for storage of information such as computer readable instructions, data structures, program modules or other data. System memory 304, removable storage 308, and non-removable storage 310 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Computing device 300 can be communicatively coupled to the cameras (e.g., cameras 120 of FIGS. 1A and 1B), inertial measurement unit (e.g., inertial measurement unit 130 of FIGS. 1A and 1B and 2), lens (e.g., lens 150 of FIG. 1A), near eye display (e.g., near eye display 190 of FIG. 1A), (and any additional devices (not shown)) and can be configured to send, receive, process, and/or analyze data to/from those devices. According to one implementation, computing device 300 can be wirelessly coupled to the above devices via wireless communication transceiver(s) operating any suitable protocol for supporting wireless (e.g., wireless USB, ZigBee, Bluetooth, Wi-Fi, etc.) In accordance with another implementation, computing device 300 can be wirelessly coupled to a network comprising one or more devices, which, in turn, can be configured to collect data from the other constituent sensors and/or devices and deliver it to computing device 300.

Wireless communication transceiver(s) can include any device suitable for supporting wireless communication between one or more components. As explained above, wireless communication transceiver(s) can be configured for operation according to any number of suitable protocols for supporting wireless, such as, for example, wireless USB, ZigBee, Bluetooth, Wi-Fi, or any other suitable wireless communication protocol or standard. According to one implementation, wireless communication transceiver can embody a standalone communication module. As such, wireless communication transceiver can be electrically coupled to computing device 300 via USB or other data communication link (e.g., network connection(s) 316) and configured to deliver data received therein to computing device 300 for further processing/analysis. According to other implementations, wireless communication transceiver can embody an integrated wireless transceiver chipset, such as the Bluetooth, Wi-Fi, NFC, or 802.11x wireless chipset included as part of computing device 300.

Network connection(s) 316 can include one or more components configured to transmit and receive data via a communication network, such as a wide area network, the Internet, a local area network, a workstation peer-to-peer network, a direct link network, a wireless network, or any other suitable communication platform. For example, network connection(s) 316 can include one or more modulators, demodulators, multiplexers, demultiplexers, network communication devices, wireless devices, antennas, modems, and any other type of device configured to enable data communication via a communication network. According to one implementation, network connection(s) 316 can be coupled to or include wireless communication devices, such as a module or modules configured to transmit information wirelessly using Wi-Fi or Bluetooth wireless protocols. Alternatively or additionally, network connection(s) 316 can be configured for coupling to one or more peripheral communication devices, such as wireless communication transceiver.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An augmented reality (AR) system, comprising:
    a frame;
    a lens attached to the frame;
    a plurality of cameras attached to the frame, wherein the cameras are configured to record a real-time image, wherein the real-time image includes a portion of a subject's body;
    a plurality of inertial measurement units, wherein a respective inertial measurement unit is attached to each respective camera; and
    a computing device including a processor and a memory operably coupled to the processor, wherein the memory has computer-executable instructions stored thereon that, when executed by the processor, cause the processor to:
        receive image data related to the portion of the subject's body;
        register the image data with the real-time image;
        track pose changes of an object of interest in real time;
        update the image data based on the tracked pose changes of the object of interest; and
        merge the updated image data with the real-time image, wherein the image data includes an anatomic structure and wherein the anatomic structure is not visible in a surgical field.

2. The AR system of claim 1, further comprising a plurality of light-emitting or light-reflecting elements, wherein a respective set of light-emitting or light-reflecting elements is attached to each respective camera.

3. The AR system of claim 1, further comprising a plurality of light-detecting elements, wherein a respective set of light-detecting elements is attached to each respective camera.

4. The AR system of claim 1, wherein each inertial measurement unit comprises at least one of a gyroscope, an accelerometer, or a magnetometer.

5. The AR system of claim 1, wherein the memory has computer-executable instructions stored thereon that, when executed by the processor, cause the processor to:
receive a respective signal from each of the inertial measurement units;
calculate a respective pose of each of the cameras relative to a reference coordinate system; and
apply a correction to the real-time image based on the respective pose of each of the cameras.

6. The AR system of claim 1, wherein the memory has computer-executable instructions stored thereon that, when executed by the processor, cause the processor to receive a respective signal from each of the cameras.

7. The AR system of claim 1, wherein the image data comprises two-dimensional or three-dimensional image data.

8. The AR system of claim 1, wherein the image data comprises magnetic resonance image (MRI), computed tomography (CT), ultrasound, or fluoroscopic image data.

9. The AR system of claim 1, wherein the image data further includes a virtual anatomic model, a virtual surgical instrument, a virtual surgical planning trajectory or angle, a template, or a surgical target relative to the anatomic structure.

10. The AR system of claim 1, wherein the anatomic structure is at least one of a blood vessel, a nerve, or a bone.

11. The AR system of claim 1, wherein the memory has computer-executable instructions stored thereon that, when executed by the processor, cause the processor to enhance the anatomic structure.

12. The AR system of claim 1, wherein the image data is registered with the real-time image based on a fiducial marker that appears in the image data and the real-time image.

13. The AR system of claim 1, wherein the image data is registered with the real-time image using a registration algorithm.

14. The AR system of claim 1, further comprising an optical projector attached to the frame or the lens, wherein the optical projector is configured to project the image data onto the lens.

15. The AR system of claim 14, wherein the lens comprises a waveguide.

16. The AR system of claim 1, wherein the memory has computer-executable instructions stored thereon that, when executed by the processor, cause the processor to:
receive pose data related to a surgical instrument or an anatomic feature relative to the portion of the subject's body;
update the image data in real-time with the pose data; and
register the updated image data with the real-time image.

17. The AR system of claim 16, wherein the pose data is obtained by an optical or electromagnetic (EM) tracking system.

18. The AR system of claim 16, wherein the pose data is obtained by tracking, using the cameras, one or more fiducial markers appearing in the real-time image.

19. The AR system of claim 16, further comprising an optical projector attached to the frame or the lens, wherein the optical projector is configured to project the registered image data onto the lens.

20. The AR system of claim 19, wherein the lens comprises a waveguide.

21. The AR system of claim 16, further comprising a display attached to the frame or the lens, wherein the display is configured to show the registered image data.

22. The AR system of claim 1, wherein the frame comprises a flexible material.

23. The AR system of claim 22, wherein the lens is at least partially transparent.

24. The AR system of claim 1, wherein the cameras are arranged in a spaced apart relationship on the frame.

25. The AR system of claim 24, wherein a respective field of view of each of the cameras intersect with one another.

26. The AR system of claim 1, further comprising at least one of a speaker or microphone.

27. An augmented reality (AR) system, comprising:
a frame;
a lens attached to the frame;
a plurality of cameras attached to the frame, wherein the cameras are configured to record a real-time image, wherein the real-time image includes a portion of a subject's body;
a plurality of inertial measurement units, wherein a respective inertial measurement unit is attached to each respective camera; and
a computing device including a processor and a memory operably coupled to the processor, wherein the memory has computer-executable instructions stored thereon that, when executed by the processor, cause the processor to:
receive image data related to the portion of the subject's body, wherein the image data includes an anatomic structure;
register the image data with the real-time image;
track pose changes of an object of interest in real time;
update the image data based on the tracked pose changes of the object of interest;
merge the updated image data with the real-time image; and
enhance the anatomic structure.

28. An augmented reality (AR) system, comprising:
a frame;
a lens attached to the frame;
a plurality of cameras attached to the frame, wherein the cameras are configured to record a real-time image, wherein the real-time image includes a portion of a subject's body;
a plurality of inertial measurement units, wherein a respective inertial measurement unit is attached to each respective camera; and
a computing device including a processor and a memory operably coupled to the processor, wherein the memory has computer-executable instructions stored thereon that, when executed by the processor, cause the processor to:
receive image data related to the portion of the subject's body;
receive pose data related to a surgical instrument or an anatomic feature relative to the portion of the subject's body;
update the image data in real-time with the pose data; and register the updated image data with the real-time image.

29. The AR system of claim 28, wherein the pose data is obtained by an optical or electromagnetic (EM) tracking system.

30. The AR system of claim 28, wherein the pose data is obtained by tracking, using the cameras, one or more fiducial markers appearing in the real-time image.

31. The AR system of claim 28, further comprising an optical projector attached to the frame or the lens, wherein the optical projector is configured to project the registered image data onto the lens.

32. The AR system of claim 31, wherein the lens comprises a waveguide.

33. The AR system of claim 28, further comprising a display attached to the frame or the lens, wherein the display is configured to show the registered image data.

34. The AR system of claim 28, further comprising a plurality of light-emitting or light-reflecting elements, wherein a respective set of light-emitting or light-reflecting elements is attached to each respective camera.

35. The AR system of claim 28, further comprising a plurality of light-detecting elements, wherein a respective set of light-detecting elements is attached to each respective camera.

36. The AR system of claim 28, wherein each inertial measurement unit comprises at least one of a gyroscope, an accelerometer, or a magnetometer.

37. The AR system of claim 28, wherein the image data comprises two-dimensional or three-dimensional image data.

38. The AR system of claim 28, wherein the image data comprises magnetic resonance image (MRI), computed tomography (CT), ultrasound, or fluoroscopic image data.

39. The AR system of claim 28, wherein the image data includes a virtual anatomic model, a virtual surgical instrument, a virtual surgical planning trajectory or angle, a template, or a surgical target relative to the anatomic structure.

40. The AR system of claim 28, wherein the image data includes an anatomic structure, and wherein the anatomic structure is at least one of a blood vessel, a nerve, or a bone.

41. The AR system of claim 28, wherein the image data is registered with the real-time image based on a fiducial marker that appears in the image data and the real-time image.

42. The AR system of claim 28, wherein the image data is registered with the real-time image using a registration algorithm.

* * * * *